(12) United States Patent
Wilcox (10) Patent No.: US 12,112,367 B2
(45) Date of Patent: Oct. 8, 2024

(54) VISUALIZATION OF GARMENTS ON A BODY MODEL OF A HUMAN

(71) Applicant: Clothing Tech LLC, Austin, TX (US)

(72) Inventor: William Wilcox, Austin, TX (US)

(73) Assignee: CLOTHING TECH LLC, Austin, TX (US)

( * ) Notice: Subject to any disclaimer, the term of this patent is extended or adjusted under 35 U.S.C. 154(b) by 89 days.

(21) Appl. No.: 17/584,710

(22) Filed: Jan. 26, 2022

(65) Prior Publication Data

US 2022/0148074 A1 May 12, 2022

Related U.S. Application Data

(62) Division of application No. 16/863,802, filed on Apr. 30, 2020, now Pat. No. 11,593,869.

(51) Int. Cl.
| | |
|---|---|
| *G06T 19/00* | (2011.01) |
| *G06Q 30/0601* | (2023.01) |
| *G06Q 50/00* | (2012.01) |
| *G06T 7/73* | (2017.01) |
| *G06T 13/40* | (2011.01) |
| *G06T 19/20* | (2011.01) |

(52) U.S. Cl.
CPC ......... *G06Q 30/0643* (2013.01); *G06Q 50/01* (2013.01); *G06T 7/74* (2017.01); *G06T 13/40* (2013.01); *G06T 19/006* (2013.01); *G06T 19/20* (2013.01); *G06T 2207/10028* (2013.01)

(58) Field of Classification Search
CPC ...... G06Q 30/0643; G06Q 50/01; G06T 7/74; G06T 13/40; G06T 19/006; G06T 19/20; G06T 2207/10028; G06T 7/75; G06T 17/00; G06T 2200/04; G06T 2207/30196; G06T 2210/16; G06T 19/00; A61B 5/0064; A61B 5/1079; A61B 5/744
See application file for complete search history.

(56) References Cited

U.S. PATENT DOCUMENTS

| | | | |
|---|---|---|---|
| 10,121,189 B2 | 11/2018 | Adeyoola et al. | |
| 2008/0180448 A1 | 7/2008 | Anguelov et al. | |
| 2010/0190610 A1* | 7/2010 | Pryor | G06Q 30/06 482/8 |
| 2015/0154691 A1 | 6/2015 | Curry et al. | |
| 2016/0227854 A1* | 8/2016 | Ellis | G06T 3/08 |
| 2019/0035149 A1 | 1/2019 | Chen et al. | |

(Continued)

FOREIGN PATENT DOCUMENTS

| | | |
|---|---|---|
| CN | 102982578 A | 3/2013 |
| CN | 103597519 A | 2/2014 |

(Continued)

OTHER PUBLICATIONS

Brett Allen et al., "Articulated body deformation from range scan data", ACM Transactions on Graphics, vol. 21, Issue 3, Jul. 3, 2002 pp. 612-619.

(Continued)

*Primary Examiner* — Chong Wu
(74) *Attorney, Agent, or Firm* — Maschoff Brennan (57) ABSTRACT

The invention relates to two computer implemented methods providing virtual fitting room functionality to a human. The two computer implemented methods allow for a simple and efficient garment selection process by the human.

7 Claims, 6 Drawing Sheets

(56) References Cited

U.S. PATENT DOCUMENTS

2019/0043269 A1  2/2019  Lin et al.
2019/0122424 A1* 4/2019  Moore .................. G06T 7/62
2019/0340803 A1  11/2019 Comer

FOREIGN PATENT DOCUMENTS

| CN | 105006014 A | 10/2015 |
|---|---|---|
| CN | 106502399 A | 3/2017 |
| CN | 108537888 A | 9/2018 |
| EP | 3 314 577 A1 | 5/2018 |
| WO | 2016/207311 A1 | 12/2016 |

OTHER PUBLICATIONS

Naoufe Werghi, "Segmentation and Modeling of Full Human Body Shape From 3-D Scan Data: A Survey", IEEE Transactions on Systems, Man, and Cybernetics, Part C, Applications and Reviews, vol. 37, Issue 6, Nov. 2007, pp. 1122-1136.
Partial European Search Report and Search opinion mailed Sep. 29, 2021 in corresponding EP Application No. 21170763.3 pp. 17.
CN Office Action dated Oct. 7, 2023 as received in Application No. 202110442289.2.
Zhang Yufei et al., "Industrial Design Based Virtual Clothing Customisation Microfactory," Industrial Design Research, 5th Series, pp. 218-222 (Oct. 31, 2017).
CN Decision to Grant dated Apr. 11, 2024 as received in Application No. 202110442289.2.

* cited by examiner

VISUALIZATION OF GARMENTS ON A BODY MODEL OF A HUMAN

CROSS REFERENCE TO RELATED APPLICATIONS

This patent application is a division of U.S. Ser. No. 16/863,802 filed Apr. 30, 2020, the contents of which are hereby incorporated herein by reference in its entirety and for all purposes.

FIELD OF THE INVENTION

The present invention relates to three computer implemented methods for visualizing garments on a body model of a human.

BACKGROUND

Choosing a right garment is often a difficult choice for a human. Conventionally, a human wanting to buy a garment must try on a number of different sizes of the garment to determine which size fits in the best way. The relationship between a nominal size of a garment and the actual size of the garment typically depends on the brand selling the garment. A human wanting to buy a garment therefore typically cannot trust the size information provided with the garment; instead, it is often necessary to try on the garment.

The entire process of finding a right garment is therefore time-consuming for the human wishing to buy a garment. Typical recommendation systems known in the prior art use height and weight of a human to propose a potentially suitable size of a garment. Neither height nor weight, however, describe the specific body shape of the human. Offering simple templates to choose from, each template describing a body shape, also leads to suboptimal size results as the specific body shape of a human may not be pre-stored. Such simple known templates furthermore cannot take into account potential movements of the human; movements, however, can strongly influence the wearing comfort and fit of a garment.

It is therefore an objective of the present invention to provide three computer implemented methods providing an improved garment selection process for a human.

It is a further objective of the present invention to provide virtual fitting room services to a human.

SUMMARY

The invention relates to a first computer implemented method, with program code being stored on a machine readable medium or embodied as an electromagnetic wave, for generating a fully animatable body model of a human for garment fitting purposes. The first computer implemented method comprises the following steps: 1) providing a pose instruction to the human, the pose instruction instructing the human to pose in at least a first and a second nominal body pose 2) receiving at least a plurality of first 3D points being based on first scan data representing a surface of the human while in a first actual body pose and a plurality of second 3D points being based on second scan data representing a surface of the human while in a second actual body pose, the at least first and second actual body pose respectively corresponding to the at least first and second nominal body pose 3) determining at least a first and a second kinematic tree from respectively the at least first and second scan data, the at least first and second kinematic tree respectively corresponding to the at least first and second actual body pose 4) establishing a one-to-one correspondence between at least a part of the first 3D points and at least a part of the second scanned 3D points 5) determining an interpolating model between the at least first and second actual body pose, wherein the interpolating model takes at least a third kinematic tree as input, wherein the interpolating model is constrained by the one-to-one correspondence, and 6) providing the interpolating model as the fully animatable body model to a computer program configured to provide virtual fitting room services.

The pose instruction tells the human to pose in at least two different body poses. Posing in different body poses is beneficial if a fully animatable body model is to be derived using scan data. A fully animatable body model is a body model that can be deformed in natural ways, i.e. typical deformations of a human can be mimicked by the fully animatable body model. The fully animatable body model is to be derived for the human that is scanned in the at least two different body poses. The scan data are 3D point data and capture information about a surface of the human. Surfaces may be the human skin or some garment worn by the human. The scan data are provided for at least two different body poses. The first 3D points and the second 3D points may be pre-processed data obtained from raw scan data.

To obtain a fully animatable body model from scan data, at least two kinematic trees are extracted from the scan data, the at least two kinematic trees corresponding to the at least two different body poses. A kinematic tree comprises nodes and edges between the nodes. The nodes may be identified with important joints of the human body, for example, while the length of the edges reflects the length of limbs, for example. Angles between edges are important as they reflect the specific body pose of the human. A kinematic tree may correspond to the human skeleton. Each extracted kinematic tree corresponds to one body pose of the human. To each kinematic tree are associated the 3D points based on the scan data, the kinematic tree being extracted from the 3D points. Since the fully animatable body model according to the invention is an interpolating model, a one-to-one correspondence between 3D points across different scan data corresponding to different scanned body poses is established. A 3D point on the left knee, for example, may be identified in scan data obtained from scanning different body poses. Using at least a third kinematic tree as input to the interpolating model and constraining the interpolating model by the one-to-one correspondence between 3D points, a mapping is learned which learns to interpolate between scanned body poses. The third kinematic tree may be equivalent to the first kinematic tree or to the second kinematic tree.

In case a 3D point is present in the 3D points corresponding to a body pose and the corresponding 3D point is missing in different 3D points corresponding to a different body pose, the missing 3D point may need to be interpolated using neighboring 3D points, for example by using smoothness constraints which are natural for a surface of a human.

Nominal body poses differ from actual body poses. Even if told which body pose to take, the actual body pose of the human will deviate from the nominal body pose. For the sake of realism, it is beneficial to extract kinematic trees using scan data corresponding to actual body poses. Nominal body pose information, however, may be used for guiding a kinematic tree determination from scan data, in particular in case large occlusions preclude a full observation of the human.

The fully animatable body model is specifically tailored to a single human. The model is therefore more realistic than body models using only height and weight as input parameters.

A virtual fitting room is the virtual equivalent of a fitting room, i.e. a human may desire to identify a suitable garment in both the virtual fitting room and the fitting room. A virtual fitting room preferentially replicates the customization experience of the fitting room. To achieve such a goal, a close virtual replica of the human may be used. The first computer implemented method according to the invention provides such a close replica, wherein the fully animatable body model also captures surface deformations of the human during movement, for example. Using the fully animatable body model, a more realistic visualization of the interactions between garments and the virtual body model is feasible. Virtual fitting room services may comprise optimal size determination of a garment for a specific human, for example.

In an embodiment of the first computer implemented method, the at least first and second scan data are provided by marker-free scanning, i.e. no additional markers are attached to the human during scanning providing the at least first and second scan data.

Placing no markers on the human during scanning simplifies and accelerates the overall scanning process, leading to an overall higher satisfaction for the human who is scanned.

In a further embodiment of the first computer implemented method, the determination of the at least first and second kinematic tree is done using a neural network, wherein the neural network is trained for extracting a kinematic tree from a scan data.

In a further embodiment of the first computer implemented method, the pose instruction instructs the human to pose in at least a first and a second nominal body pose corresponding to common body poses of the human, wherein the human is free to choose the at least first and second nominal body pose.

The interpolating model, the interpolating model being the fully animatable body model, typically shows more realistic behavior close to scanned body poses. The interpolating model degrades if evaluated for body poses far away from scanned body poses used for learning the interpolating model. The human may therefore choose the body poses which are scanned to ensure that the fully animatable body model is realistic for typical use cases as envisioned by the scanned human. An automatic garment fitting process provided by a virtual fitting room, for example, may use the realistic behavior of the fully animatable body model near body poses commonly encountered by the scanned human to provide for better fitting garments adapted to the needs of the scanned human.

In a further embodiment of the first computer implemented method, the at least first and second scan data capture the human in a dressed state, wherein the human is allowed to freely choose a worn dress.

The scan data may be acquired by a millimeter wave scanner, for example. In this case, the scan data comprise 3D skin surface points of the scanned human. The raw scan data may be pre-processed before providing them to the first computer implemented method. Scanning a human in a dressed state simplifies and accelerates the entire scanning process, leading to a higher satisfaction for the scanned human.

The invention also relates to a second computer implemented method, with program code being stored on a machine readable medium or embodied as an electromagnetic wave, for determining a best fitting garment for a human. The second computer implemented method comprises the following steps: 1) establishing access to a stored garment catalogue comprising a plurality of 3D garment digital twins (GDT), each GDT associated to at least one of a plurality of garment types 2) receiving a body model of the human 3) receiving a garment instruction from the human about a chosen garment type via a graphical user interface, the chosen garment type being one of the plurality of garment types 4) determining a best fitting garment according to a best fitting criterion based on the GDTs associated to the chosen garment type and the body model of the human 5) providing the human with information about the best fitting garment via the graphical user interface, and 6) visualizing the best fitting garment on the body model in a virtual 3D environment.

A human may desire to buy a new garment. Instead of visiting a clothing store to try on new garments, the human may desire to accelerate the entire selection process. The second computer implemented method according to the invention is able to access a stored garment catalogue. The stored garment catalogue comprises a plurality of 3D garment digital twins (GDT), each GDT being a highly realistic 3D model of an actual garment. Each GDT comprises sufficient information for virtually determining the physical behavior in case the GDT is placed on the body model of the human. A GDT may therefore comprise fabric information and/or seam information, for example. The plurality of GDTs in the stored garment catalogue may be grouped using garment types. Garment types may be categories such as trousers or shirts, for example, or subcategories such as jeans, or even finer subcategories specifying a jeans and its color, for example. As such, a GDT may be associated to a plurality of garment types.

The human wishing to identify a suitable garment instructs the computer program providing the second computer implemented method about a chosen garment type. The instruction proceeds via a graphical user interface. Using a best fitting criterion, the GDT which minimizes the best fitting criterion is selected from the list of GDTs associated to the chosen garment type. To be amenable to a computer program, the best fitting criterion provides a numerical output value. The human is instructed about the best fitting GDT. The best fitting GDT is simulated in a physically realistic way on the body model of the human. The simulation is displayed in a virtual 3D environment, for example a computer aided design (CAD) program, to the human.

Using a threshold value, the computer program providing the second computer implemented method may determine that no GDT associated to the chosen garment type fits the human well enough. Such an operation may be provided by comparing the numerical output value provided by the best fitting criterion with the threshold value. The threshold value may depend on the best fitting criterion. The computer program may instead select a closely related garment type to the chosen garment type and attempt to find a suitable best fitting GDT associated to the closely related garment type. For example, if the human chooses as garment type "blue jeans", a closely related garment type may be "black jeans", for example. In case garment types are structured in a polytree, for example, closeness of garment types may be automatically determined by distances in the polytree.

In an embodiment of the second computer implemented method, the best fitting criterion comprises at least two sub-criteria, wherein each sub-criterion uses a measured model property of the body model and a corresponding measured garment property of at least one of the GDTs associated to the chosen garment type, and each sub-criterion comprises a metric for comparing the measured model property with the measured garment property, the metric providing a discrepancy, wherein the best fitting garment according to the best fitting criterion is determined to be the garment that minimizes a combination of discrepancies provided by the sub-criteria.

The best fitting criterion may comprise sub-criteria. Since both the body model and the GDTs are geometric, measurements providing numerical values may be carried out on them. For example, waist circumference is a measured model property of the body model. In case of a jeans as GDT, for example, a measured garment property corresponding to waist circumference can be determined. Each measured model property is compared to the correspondingly obtained measured garment property, the comparison providing a discrepancy value. A sub-criterion provides a discrepancy value, the discrepancy value being a numerical output. In case the measured model property is the length of the upper arm and the corresponding measured garment property is the sleeve length of a t-shirt, for example, the discrepancy value may be the absolute value of the difference of the two terms, for example. In case the best fitting criterion comprises a plurality of sub-criteria, the overall best fitting criterion is a combination of the sub-criteria. A simple combination, for example, is a linear weighted sum of the sub-criteria, wherein the weight of each sub-criterion measures its overall importance.

In a further embodiment of the second computer implemented method, the best fitting criterion is provided by the human via the graphical user interface.

The notion of "best fitting" is highly subjective. The human may therefore provide the best fitting criterion via the graphical user interface to the computer program providing the second computer implemented method. A possible list of best fitting criteria may also be provided to the human, and the human may choose a best fitting criterion from the provided list of best fitting criteria. Alternatively, if no best fitting criterion is specified by the human, a chosen garment type may be by default automatically connected to a best fitting criterion. Different garment types may cater to different customer groups, implying that a garment type may be explicitly associated to a specific way of wearing it. Such information may be encoded in the best fitting criterion which is connected to a garment type by default.

In a further embodiment of the second computer implemented method, the visualization of the best fitting garment on the body model comprises vanity visualization functionality, wherein a horizontal extent of the body model and of the best fitting garment is changed by the vanity visualization functionality.

During visualization of the best fitting garment on the body model, both the body model and the best fitting garment may be altered so as to make the entire visualization more pleasing to the human. For example, the waist region may be slimmed for females, and the shoulder region may be made broader for males.

In a further embodiment of the second computer implemented method, the human is provided with the option to choose a next larger or a next smaller garment compared to the best fitting garment, wherein the next larger or the next smaller garment is visualized on the body model in the virtual 3D environment.

The human's subjective comfort may be increased by verifying the garment selection provided by the computer program providing the second computer implemented method. Verification may proceed by looking at the next smaller or next larger garment compared to the best fitting garment, provided they exist.

In a further embodiment of the second computer implemented method, the body model is provided as a fully animatable body model by the first computer implemented method.

In case the body model is rigid, no physically realistic interaction between a garment and the body model may be determined during body movement, for body movement cannot be properly simulated using a rigid body model. A fully animatable body model may be used for such purposes, however, as the deformation of a garment during movement may be simulated.

The invention also relates to a third computer implemented method, with program code being stored on a machine readable medium or embodied as an electromagnetic wave, for visualizing at least one garment on a fully animatable body model of a human. The third computer implemented method comprises the following steps: 1) receiving the fully animatable body model of the human 2) receiving a pose display instruction via a graphical user interface 3) receiving a garment digital twin of the at least one garment, and 4) visualizing the garment digital twin on the fully animatable body model, wherein the fully animatable body model is adopting a pose according to the pose display instruction, wherein the garment digital twin is deformed due to the pose of the fully animatable body model, the deformation taking into account at least gravity, fabric properties of a fabric of the garment, and geometric constraints imposed by the fully animatable body model in the pose according to the pose display instruction on the garment digital twin.

The pose display instruction received via a graphical user interface specifies in which pose the fully animatable body model is to be positioned. The GDT is placed on the fully animatable body model and deformed in a physically realistic manner.

In an embodiment of the third computer implemented method, the pose display instruction is provided in parallel to the visualization, wherein a body scanner captures a pose of the human, wherein the captured pose is provided as pose display instruction.

A body scanner may record a pose of the human whose fully animatable body model is available to the computer program providing the third computer implemented method. From the scanned pose a kinematic tree may be extracted and used as input to the fully animatable body model, providing a deformation of the fully animatable body model mimicking the pose of the human.

In a further embodiment of the third computer implemented method, the pose display instruction captures a real-time motion of the human, wherein the visualization of the at least one garment on the fully animatable body model follows the real-time motion in parallel.

A body scanner may record real-time motion of the human whose fully animatable body model is available to the computer program providing the third computer implemented method. From the real-time motion a real-time kinematic tree may be extracted and used as input to the fully animatable body model, providing a real-time deformation of the fully animatable body model mimicking the real-time motion of the human. The interaction of the GDT with the fully animatable body model controlled in real time is simulated in real time as well.

In a further embodiment of the third computer implemented method, the fully animatable body model is provided by the first computer implemented method.

In a further embodiment of the third computer implemented method, the garment digital twin is provided by the second computer implemented method.

In an embodiment of the second or third computer implemented method, the human is provided with the option of sharing the fully animatable body model in a dressed state via social media, and wherein the computer implemented method is able to receive feedback from external sources via social media.

A human wishing to buy a new garment in conventional clothing stores is often accompanied by other humans that give commentary about the style, how it looks, how it fits etc. Such commentary functionality may be provided by the computer program providing the second computer implemented method and/or the computer program providing the third computer implemented method. While virtually trying on a garment, the human may be provided with the option to share images or movies in 2D or 3D of the virtually worn garment with their connections on social media in order to solicit input and feedback on the garment or on combinations of worn garments.

BRIEF DESCRIPTION OF THE DRAWINGS

The inventive system is described below in more detail purely by way of example with the aid of concrete exemplary embodiments illustrated schematically in the drawings, further advantages of the invention also being examined. Identical elements are labelled with the same reference numerals in the figures. In detail.

DETAILED DESCRIPTION

Figure 1:
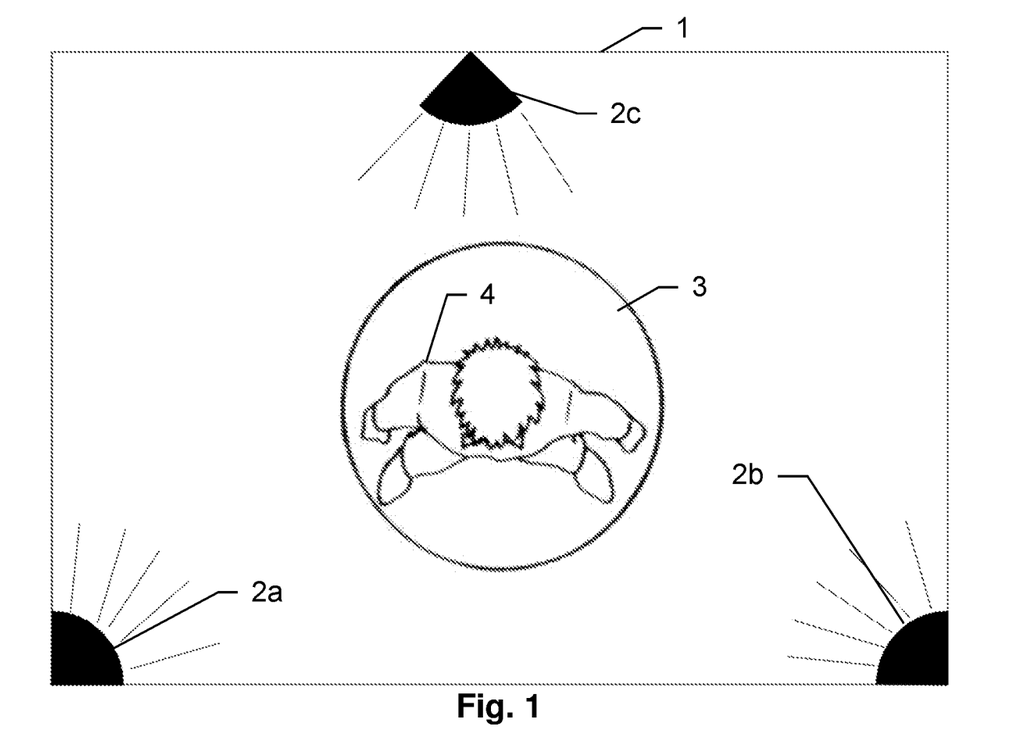
FIG. 1 shows a schematic and illustrative depiction of a full body scanner scanning a human.

FIG. 1 shows a schematic and illustrative depiction of a full body scanner scanning a human, the scene shown in a top-down view. Scanners 2a,2b,2c are mounted on the wall of a room 1, in particular a fitting room. In the exemplary embodiment of FIG. 1, three scanners are shown. The number of scanners, however, is arbitrary, and is in particular equal to eight. The scanners may be preferentially configured to be added to existing fitting rooms. A visual indication 3 signals to a human 4 where to stand during scanning. The scanners 2a,2b,2c may be embodied as millimeter wave scanners or as infrared scanners, for example. Each of the scanners 2a,2b,2c outputs scan data comprising 3D points. The 3D points may be pre-processed, the pre-processing for example comprising de-noising. From the scan data, a mesh of the captured body shape may be extracted. Since the size of fitting rooms may vary, the scanners 2a,2b,2c are preferentially calibrated after mounting them in a fitting room. The calibration process may allow for fusing captured data from the different scanners 2a,2b, 2c, the fused data being the scan data provided by the full body scanner. The scan data comprise 3D points of a surface of the human 4. The number of scanners and their positions in the fitting room may preferentially be such that each part of the human 4 may be seen from at least one of the scanners. The scanners 2a,2b,2c preferentially capture a shape of the human in one or two seconds.

The scanners 2a,2b,2c may image the human 4 in a dressed state. Millimeter wave scanners, for example, "see through" worn clothing, i.e. such scanners provide actual surface data of the human 4.

Figure 2:
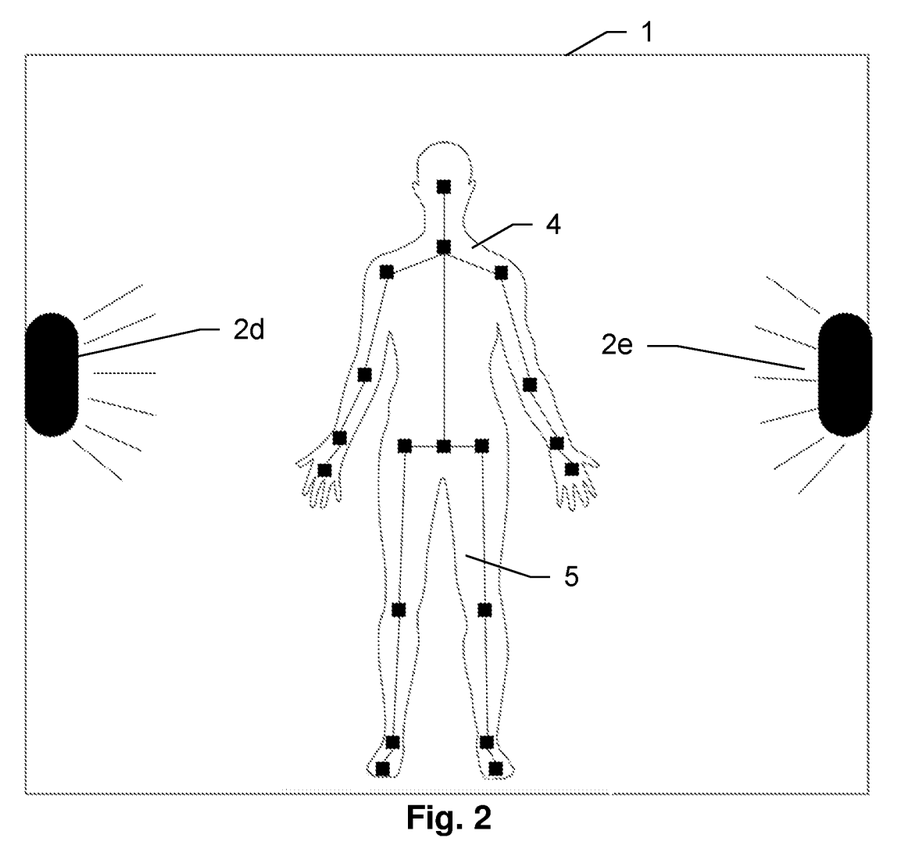
FIG. 2 shows a schematic and illustrative depiction of a full body scanner scanning a human and a kinematic tree derived from scan data.

FIG. 2 shows a schematic and illustrative depiction of a full body scanner scanning a human and a kinematic tree derived from scan data, the scene shown in a side view. As in FIG. 1, scanners 2d,2e are mounted on the wall of a room 1, in particular a fitting room, the scanners 2d,2e scanning a human 4. The data captured by the scanners 2d,2e are fused, the fusion providing scan data. Based on the scan data, processed 3D points may be extracted, for example by pre-processing the scan data. From the 3D points, a kinematic tree 5 is obtained, wherein the kinematic tree 5 represents a pose of the human 4 during scanning. The number of nodes of the kinematic tree may be fixed, or it may be changed depending on the scan data. The kinematic tree 5 may be extracted using a neural network, for example. The human 4 may preferentially be scanned marker-free, i.e. no additional markers are attached to the human 4 during scanning.

To provide a fully animatable body model of the human 4, the human 4 is preferentially scanned in multiple different poses. For each pose, the corresponding scan data are used for deriving a corresponding kinematic tree representing the pose. The scan data corresponding to each pose comprise 3D points of a surface of the human 4, the surface depending on the pose. The different poses during scanning preferentially represent common poses encountered during daily life of the human 4, for example standing straight with raised arms, standing straight with lowered arms etc. The fully animatable body model may be provided as an interpolating model. The interpolating model may be parametrized using at least a kinematic tree; the interpolating model is preferentially constrained by a one-to-one correspondence between 3D points corresponding to different poses. The 3D points used for establishing the one-to-one correspondence may be pre-processed raw 3D points directly obtained from the full body scanner. The one-to-one correspondence may be obtained using non-rigid registration, for example, using a least squares optimization target. The provided interpolating model works as follows: If a kinematic tree corresponding to a scanned pose is used as input for the interpolating model, the interpolating model provides the 3D points corresponding to the scanned pose as output; if a kinematic tree which does not correspond to a scanned pose is used as input for the interpolating model, the interpolating model provides 3D points as outputs corresponding to a combination of the 3D points used for constraining the interpolating model, wherein the specific combination depends on at least the input kinematic tree. The 3D points may equivalently be represented by a mesh, the mesh comprising triangles.

Besides providing a fully animatable body model, the full body scanner may also provide a rigid body model. The rigid body model may be extracted from scan data capturing the human 4 in one pose.

Each of the scanners 2d,2e may in some cases—in particular depending on its position in the fitting room 1—capture only some parts of a surface of the human 4. In such a case, before or during establishing the one-to-one correspondence, missing 3D points may need to be added, for example using smoothness constraints or other a prior knowledge.

Figure 3:
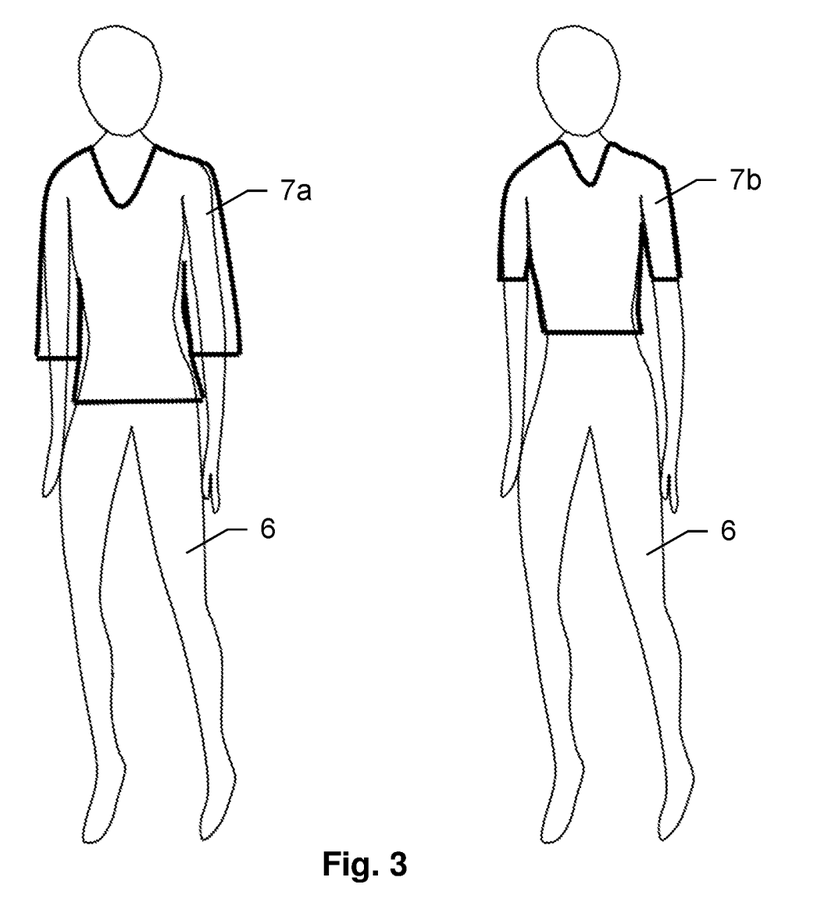
FIG. 3 shows a schematic and illustrative depiction of automatically choosing the size of a garment using a body model.

FIG. 3 shows a schematic and illustrative depiction of automatically choosing the size of a garment using a body model, in particular a rigid body model. The body model 6 of a human, the body model 6 accurately capturing the shape of the human, possesses measurable properties. Examples of such measurable properties are circumference of the waist, length of arms, width of shoulders etc. In principle, any measurement done on the body model 6 providing a numerical output may be seen as a measurable property. Corresponding measurements may be carried out on 3D garment digital twins (GDT), too. A GDT is a 3D model accurately representing a garment.

The human whose body model is used in FIG. 3 may desire to buy a well-fitting shirt with short sleeves, for example. A shirt with short sleeves is a garment type. Other garment types would be, for example, shirts with long sleeves or jeans. A garment type may also be a specific design of a jeans, for example, of a specific brand. In any case, a garment type is associated to a plurality of GDTs 7a,7b representing different sizes of the garment type, for example. Once the human has decided about a chosen garment type, the best fitting size of the chosen garment type is determined, wherein "best fitting" is determined using the GDTs 7a,7b associated to the chosen garment type and the body model 6 of the human.

The criterion of what is to be considered "best fitting" is highly subjective and strongly depends on the preferences of the human. Some people consider a tightly fitting t-shirt as desirable, for example, while others prefer looser fits. The human therefore may provide an instruction defining the meaning of "best fitting". To be usable by a computer program, it is necessary for the provided meaning of "best fitting" to be expressible in numbers. The human may be provided with a list of different "best fitting" criteria, for example, from which a "best fitting" criterion can be chosen. The "best fitting" criterion may be expressed using a combination of measurable properties of both the body model 6 and the GDTs 7a,7b associated to the chosen garment type. The corresponding best fitting size is the size that minimizes the "best fitting" criterion. An example for a "best fitting" criterion may be a weighted combination of waist, chest and shoulder discrepancy between the body model 6 and the GDTs 7a,7b. Each discrepancy may be provided by a squared difference between a measurable property of the body model 6 and the corresponding measurable property of each associated GDT 7a,7b. Using such a setup, the "best fitting" available size of the chosen garment type may be automatically determined for the human.

FIG. 3 shows an illustrative embodiment. A t-shirt is chosen as garment type by a human whose body model 6 is used by the computer program determining the best fitting size. In the illustrative embodiment, the human has chosen "tight fit" as best fitting criterion. The left subfigure of FIG. 3 shows the body model 6 and a loosely fitting t-shirt model 7a, and the right subfigure of FIG. 3 shows the body model 6 and a tightly fitting t-shirt model 7b. The computer program automatically choses the tightly fitting t-shirt model 7b, for it minimizes the "tight fit" criterion compared to the loosely fitting t-shirt model 7a.

After having determined the best fitting garment size of the chosen garment type, the best fitting garment is visualized and displayed to the human. For the visualization, the best fitting garment is placed on the body model 6.

Figure 4:
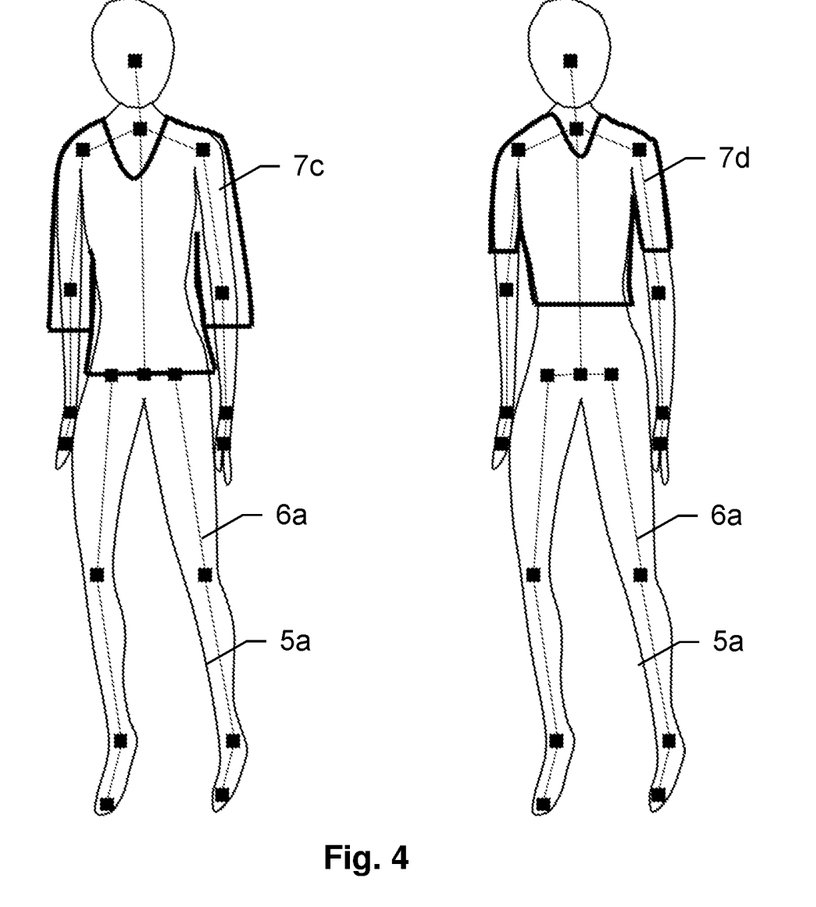
FIG. 4 shows a schematic and illustrative depiction of automatically choosing the size of a garment using a fully animatable body model.

FIG. 4 shows a schematic and illustrative depiction of automatically choosing the size of a garment using a fully animatable body model. FIG. 4 is similar to FIG. 3, the main difference being that in FIG. 3 a rigid body model 6 is used for choosing a best fitting garment while in FIG. 4 a fully animatable body model 6a is used for that purpose. To graphically show the difference, the fully animatable body model 6a is displayed together with a kinematic tree 5a representing the pose of the fully animatable body model 6a. For visualization purposes, the kinematic tree 5a is typically not displayed but instead only used for computing purposes.

Similar to FIG. 3, the best fitting garment is chosen from a list of available GDTs 7c,7d associated to a chosen garment type. In FIG. 4, only one pose of the fully animatable body model 6a is shown. The "best fitting" criterion, however, may be evaluated using a plurality of poses, each pose for example corresponding to a commonly encountered pose of the human whose fully animatable body model 6a is used.

Figure 5:
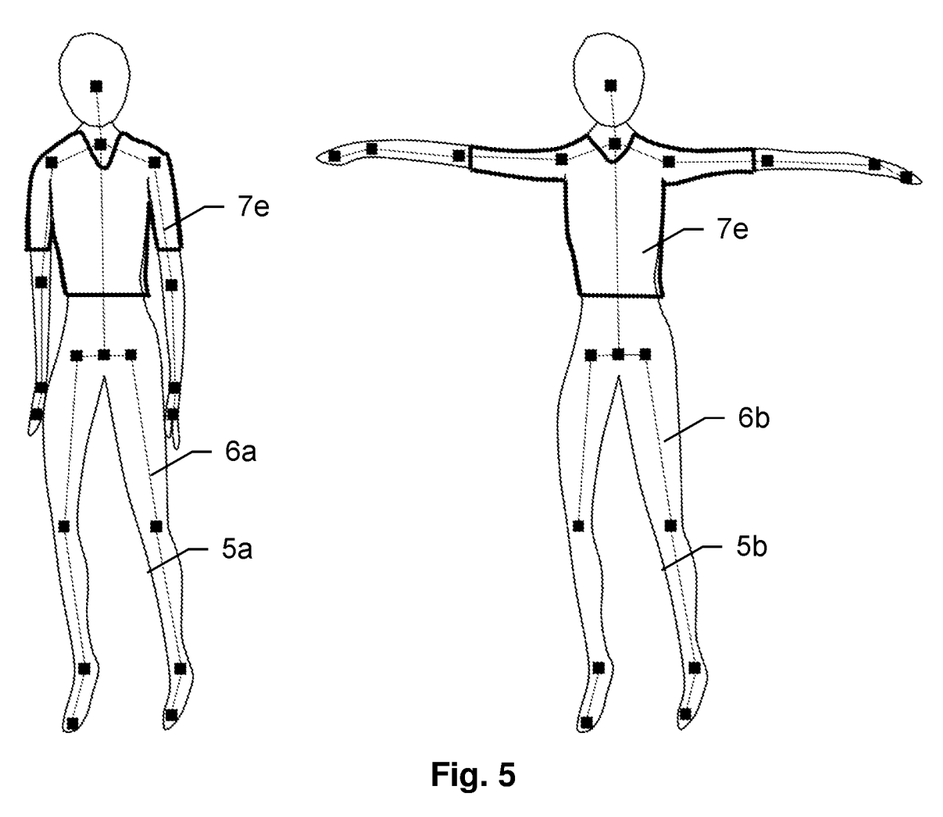
FIG. 5 shows a schematic and illustrative depiction of visualizing a garment on a fully animatable body model in different poses.

FIG. 5 shows a schematic and illustrative depiction of visualizing a garment on a fully animatable body model in different poses. A t-shirt 7e is placed on the fully animatable body model in a first pose 6a and on a fully animatable body model in a second pose 6b, for example, wherein the second pose differs from the first pose in that the arms are raised. The poses used in FIG. 5 are only exemplary, i.e. any other poses could be used as well. The fully animatable body model is a model of a human. The human is shown how the t-shirt 7e looks on the human's body in different poses. As such, the human can decide more easily about whether the t-shirt 7e fits nicely or if it does not, for example. If an image sensor tracks the human in real time, and if the captured image sensor data can be evaluated in real time, the evaluation providing a real-time kinematic tree, for example, then the fully animatable body model can be animated to follow the real-time motion of the human.

Figure 6:
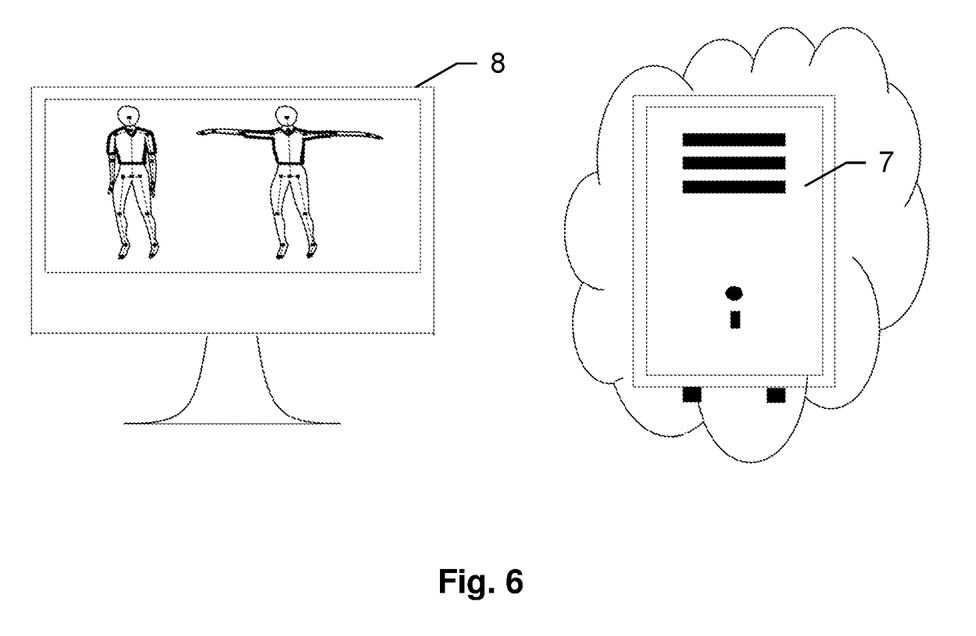
FIG. 6 shows a schematic and illustrative depiction of a computing unit and a display providing a graphical user interface.

FIG. 6 shows a schematic and illustrative depiction of a computing unit and a display providing a graphical user interface. The computing unit 7 and the display 8 may be located at physically remote locations. The computing unit 7 receives instructions from a human via a graphical user interface provided by the display 8. A rigid body model or a fully animatable body model of the human or of a different human is stored on the computing unit 7 or can be accessed by the computing unit 7 from some external storage. The human may, for example, instruct the computing unit 7 to place a garment digital twin onto the rigid body model or onto the fully animatable body model and to render the resulting dressed body model, wherein the rendered dressed body model is displayed via the graphical user interface provided by the display 8. The same computing unit 8 or a different computing unit may also have access to a full body scanner, wherein a computer program on the computing unit 8 or on the different computing unit may determine the rigid body model or the fully animatable body model using scan data provided by the full body scanner. In case the different computing unit determines the rigid body model or the fully animatable body model, the different computing unit may be connected to the computing unit 8 via a network allowing data transfer.

The disclosure further comprises the following subject matter (SM):

SM1. Computer implemented method, with program code being stored on a machine readable medium or embodied as an electromagnetic wave, for generating a fully animatable body model of a human for garment fitting purposes, the computer implemented method comprising providing a pose instruction to the human, the pose instruction instructing the human to pose in at least a first and a second nominal body pose, receiving at least a plurality of first 3D points, the first 3D points being based on first scan data representing a surface of the human while in a first actual body pose and a plurality of second 3D points, the second 3D points being based on second scan data representing a surface of the human while in a second actual body pose, the first and second actual body pose respectively corresponding to the first and second nominal body pose, determining at least a first and a second kinematic tree from respectively the at least first and second scan data, the at least first and second kinematic tree respectively corresponding to the at least first and second actual body pose, establishing a one-to-one correspondence between at least a part of the first 3D points and at least a part of the second 3D points, determining an interpolating model between the at least first and second actual body pose, wherein the interpolating model takes at least a third kinematic tree as input, wherein the interpolating model is constrained by the one-to-one correspondence, and providing the interpolating model as the fully animatable body model to a computer program configured to provide virtual fitting room services.

SM 2. Computer implemented method according to SM 1, wherein the at least first and second scan data are provided by marker-free scanning.

SM 3. Computer implemented method according to SM 1, wherein the determination of the at least first and second kinematic tree is done using a neural network, wherein the neural network is trained for extracting a kinematic tree from a scan data.

SM 4. Computer implemented method according to SM 1, wherein the pose instruction instructs the human to pose in at least a first and a second nominal body pose corresponding to common body poses of the human, wherein the human is free to choose the at least first and second nominal body pose.

SM 5. Computer implemented method according to SM 1, wherein the at least first and second scan data capture the human in a dressed state, wherein the human is allowed to freely choose a worn dress.

Although the invention is illustrated above, partly with reference to some preferred embodiments, it must be understood that numerous modifications and combinations of different features of the embodiments can be made. All these modifications lie within the scope of the appended claims.

What is claimed is:

1. Computer-implemented method for determining a best fitting garment for a human, the computer-implemented method comprising:
    establishing access to a stored garment catalogue comprising a plurality of 3D garment digital twins (GDT), each GDT associated to at least one of a plurality of garment types;
    receiving a body model of the human;
    receiving a garment instruction from the human about a chosen garment type via a graphical user interface, the chosen garment type being one of the plurality of garment types;
    determining, based on the GDTs associated to the chosen garment type and the body model of the human, a best fitting garment according to a best fitting criterion;
    providing the human with information about the best fitting garment via the graphical user interface; and
    visualizing the best fitting garment on the body model in a virtual 3D environment.

2. Computer implemented method according to claim 1, wherein the best fitting criterion comprises at least two sub-criteria, wherein each sub-criterion uses a measured model property of the body model and a corresponding measured garment property of at least one of the GDTs associated to the chosen garment type, and each sub-criterion comprises a metric for comparing the measured model property with the measured garment property, the metric providing a discrepancy, wherein the best fitting garment according to the best fitting criterion is determined to be the garment that minimizes a combination of discrepancies provided by the sub-criteria.

3. Computer implemented method according to claim 1, wherein the best fitting criterion is provided by the human via the graphical user interface.

4. Computer implemented method according to claim 1, wherein the visualization of the best fitting garment on the body model comprises vanity visualization functionality, wherein a horizontal extent of the body model and of the best fitting garment is changed by the vanity visualization functionality.

5. Computer implemented method according to claim 1, further providing the human with the option to choose a next larger or a next smaller garment compared to the best fitting garment, wherein the next larger or the next smaller garment is visualized on the body model in the virtual 3D environment.

6. Computer implemented method according to claim 1, wherein the body model is provided as a fully animatable body model by the computer implemented method according to claim 1.

7. Computer implemented method according to one of claim 1, wherein the human is provided with the option of sharing the fully animatable body model in a dressed state via social media, and wherein the computer implemented method is able to receive feedback from external sources via social media.

* * * * *